(12) United States Patent
Kamiyama et al.

(10) Patent No.: US 9,011,401 B2
(45) Date of Patent: Apr. 21, 2015

(54) DISPOSABLE DIAPER

(75) Inventors: Ryuichi Kamiyama, Kagawa (JP); Toshimitsu Baba, Kagawa (JP); Kaiyo Nakajima, Kagawa (JP); Reiko Nitta, Kagawa (JP)

(73) Assignee: Unicharm Corporation, Ehime (JP)

(*) Notice: Subject to any disclaimer, the term of this patent is extended or adjusted under 35 U.S.C. 154(b) by 814 days.

(21) Appl. No.: 13/262,143

(22) PCT Filed: Mar. 29, 2010

(86) PCT No.: PCT/JP2010/002289
§ 371 (c)(1),
(2), (4) Date: Sep. 29, 2011

(87) PCT Pub. No.: WO2010/113470
PCT Pub. Date: Oct. 7, 2010

(65) Prior Publication Data
US 2012/0041407 A1 Feb. 16, 2012

(30) Foreign Application Priority Data

Mar. 31, 2009 (JP) .................................. 2009-086573

(51) Int. Cl.
*A61F 13/15* (2006.01)
*A61F 13/20* (2006.01)
*A61F 13/496* (2006.01)
(Continued)

(52) U.S. Cl.
CPC .......... *A61F 13/496* (2013.01); *A61F 13/49011* (2013.01); *A61F 13/515* (2013.01)

(58) Field of Classification Search
CPC ................ A61F 13/539; A61F 13/496; A61F 13/49466; A61F 13/515; A61F 2013/53908; A61F 2013/53916; A61F 2013/53925
USPC ...................... 604/358, 386, 385.03
See application file for complete search history.

(56) References Cited

U.S. PATENT DOCUMENTS 6,218,593 B1 4/2001 Torimae et al.
6,635,798 B1 * 10/2003 Yoshioka et al. ............. 604/365

FOREIGN PATENT DOCUMENTS

JP 2-11067 Y2 3/1990
JP 2000-135240 A 5/2000
(Continued)

OTHER PUBLICATIONS

Supplementary European Search Report issued Mar. 13, 2014, corresponds to European patent application No. 10758250.4.
(Continued)

*Primary Examiner* — Michele M Kidwell
(74) *Attorney, Agent, or Firm* — Lowe Hauptman & Ham, LLP (57) ABSTRACT

Disposable diapers improved so that waist regions are effectively elastic to assure high fitness are provided. In a first waist region, bonding region coated with adhesive lines includes a first bonding region coated with first adhesive lines extending from a peripheral edge of a waist-opening toward a crotch region and a second bonding region coated with second adhesive lines extending from the first adhesive lines into the crotch region wherein the first adhesive lines are noncontiguous to the second adhesive lines in the direction of the longitudinal axis so that, with the diaper put on the wearer's body, a region defined in the vicinity of a boundary between the first bonding region and the second bonding region folded inward.

8 Claims, 7 Drawing Sheets

(51) Int. Cl.
*A61F 13/49* (2006.01)
*A61F 13/515* (2006.01)

(56) References Cited

FOREIGN PATENT DOCUMENTS

| JP | 2001-46426 A | 2/2001 |
| JP | 200146426 A | 2/2001 |
| JP | 3537610 B2 | 6/2004 |
| JP | 3667353 B2 | 7/2005 |
| JP | 2008-295930 A | 12/2008 |
| JP | 2009-61127 A | 3/2009 |

OTHER PUBLICATIONS

International Search Report for International Application No. PCT/JP2010/002289, mailed on May 11, 2010.

* cited by examiner

DISPOSABLE DIAPER

RELATED APPLICATIONS

The present application is a national phase of PCT/JP2010/002289 filed Mar. 29, 2011 and is based on, and claims priority from, Japanese Application Number 2009-086573, filed Mar. 31, 2009.

TECHNICAL FIELD

The present disclosure relates to disposable diapers and more particularly to disposable diapers having elastic waist regions.

BACKGROUND

Disposable diapers having elastic waist regions are known. For example, JP 3667353 B1 discloses a disposable diaper comprising an elastic sheet lying on a skin-facing side and a non-elastic sheet lying on a non-skin-facing side which are bonded to each other at plural adhesive lines extending in a longitudinal direction of the diaper so as to form a plurality of channels extending in the longitudinal direction.

In such a diaper, the waist region as a whole is elastic so as to assure good fit to the wearer's body and, in addition, the elastic sheet and the non-elastic sheet are bonded to each other through the intermediary of the plural adhesive lines extending in the direction of the longitudinal axis so as to define the channels. The plural adhesive lines extending in the longitudinal direction may provide the waist region as a whole with a uniform stiffness.

CITATION LIST

Patent Literature

[PTL 1]
Japanese Patent Publication No. 3667353 B2

SUMMARY

A disposable diaper in accordance with one or more embodiment of the present invention comprises a longitudinal axis and a transverse axis, a skin-facing side and a non-skin-facing side, and comprising a first waist region, a second waist region, a crotch region extending between the first and second waist regions, a waist-opening and a pair of leg-openings wherein at least the first waist region of the first and second waist regions is elastic.

The disposal diaper described above includes a non-elastic sheet lying on the non-skin facing side and an elastic sheet lying on the skin-facing side, the non-elastic sheet and the elastic sheet are joined together along plural adhesive lines extending in a direction of the longitudinal axis and spaced from one another in a direction of the transverse axis, the adhesive lines comprise first adhesive lines extending from or from adjacent to a peripheral edge of the waist-opening toward the crotch region and defining a first bonding region, and second adhesive lines extending from the crotch region toward the first adhesive lines and defining a second bonding region, and at least some of the second adhesive lines are noncontiguous to any of the first adhesive lines in the direction of the longitudinal axis.

DETAILED DESCRIPTION

The inventor(s) has/have found that stiffness as well as elasticity desired for a waist region depends a great deal on the particular area in the waist region, more specifically, on whether the area is an upper area or a lower area of the waist region.

Specifically, the lower areas of the front and/or rear waist regions and the crotch region are apt to get wrinkles as the wearer moves and, to prevent these lower areas from getting wrinkles, these lower areas preferably have elasticity higher than that of the upper area. In contrast, the upper areas of the front and/or rear waist regions adapted to be held by the fingers and to be pulled upward to put the diaper on the wearer's body preferably have an appropriate stiffness.

Therefore, when a plurality of adhesive lines are to be used for bonding layers of a waist region, such adhesive lines are configurable to provide differential stiffness so that the upper area and the lower area of the waist region have different levels of elasticity as desired.

Details of a diaper according to exemplary embodiments of the present invention will be more fully understood from the description given hereunder in reference to the accompanying drawings. It should be appreciated that same or similar reference numerals used in the specification designate same or similar members or regions through all specifically disclosed embodiments.

First Embodiment

FIGS. 1-4 illustrate a diaper 10 according to a first exemplary embodiment. In FIGS. 1-4, the longitudinal axis of the diaper 10 is designated by P and the transverse axis of the diaper 10 is designated by Q. The diaper 10 is symmetric about the longitudinal axis P as well as the transverse axis Q.

Figure 1:
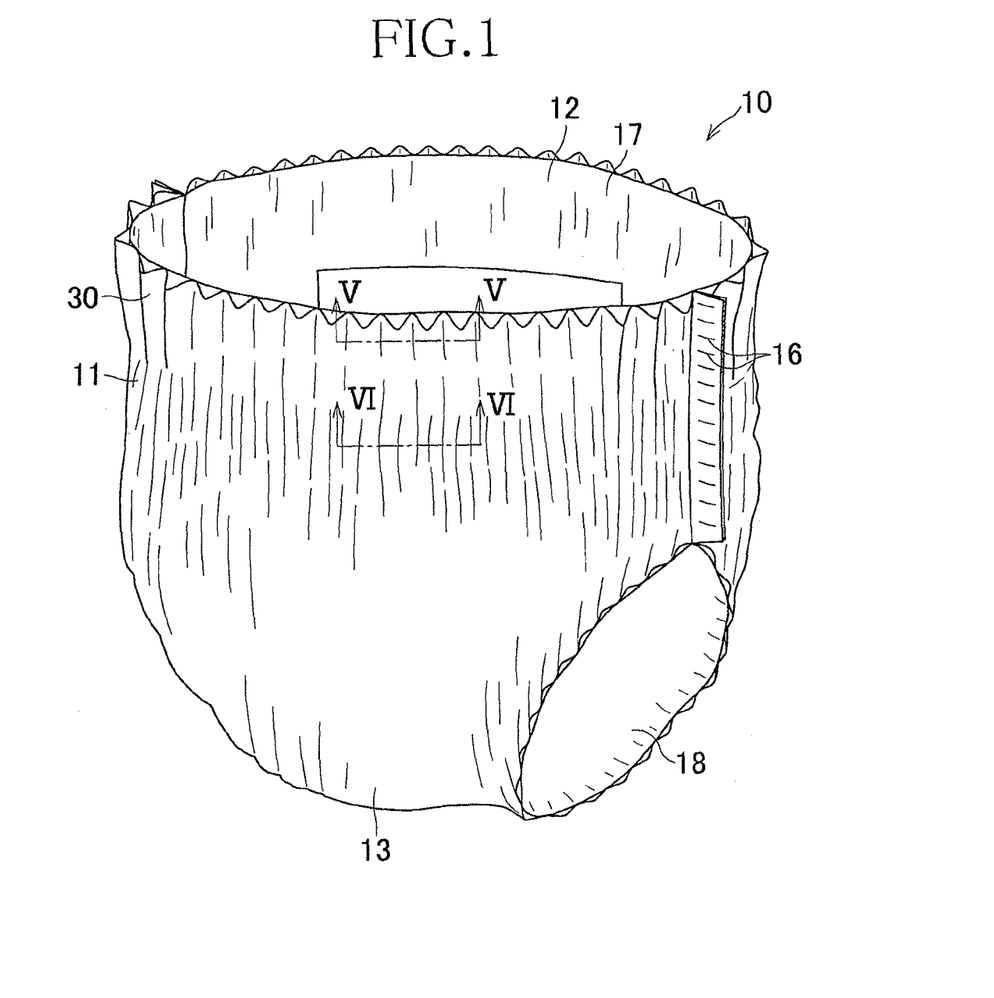
FIG. 1 is a perspective view of the diaper according to a first embodiment of the present invention.

As will be apparent from FIG. 1, the diaper 10 is defined by the longitudinal axis P, the transverse axis extending orthogonally to the longitudinal axis P, a skin-facing side and a non-skin-facing side. The diaper 10 comprises a chassis 14 and an absorbent structure 15 lying on the inner surface, i.e., the skin-facing side, of the chassis and having a rectangular shape which is elongated in the direction of the longitudinal axis P. The chassis 14 includes a front waist region 11, a rear waist region 12 and a crotch region 13 extending between these front and rear waist regions 11, 12.

The chassis 14 has front and rear ends 14a, 14b opposed to each other in the direction of the longitudinal axis P and respectively extending in the direction of the transverse axis Q and side edges 14c, 14d opposed to each other in the direction of the transverse axis Q and respectively extending in the direction of the longitudinal axis P. In the crotch region 13, the opposite side edges 14c, 14d are curved inwardly so as to be concave toward the longitudinal axis P.

The side edges 14c, 14d of the front waist region 11 and the associated side edges 14c, 14d of the rear waist region 12 are put flat, so that their inner surfaces are in a face-to-face relationship, and joined together in side seams 16 intermittently arranged in the direction of the longitudinal axis by known techniques, for example, various types of heat sealing such as hot embossing or ultrasonic sealing techniques, whereupon a waist-opening 17 and a pair of leg-openings 18 are defined (See FIG. 1). A peripheral edge of the waist-opening 17 is defined by the front and rear ends 14a, 14b of the chassis 14.

The chassis 14 comprises a preferably moisture-pervious elastic inner sheet 19 lying on the skin-facing side, i.e., the side facing the wearer's skin in use, and preferably formed of an elastic fibrous non-woven fabric or an elastic perforated plastic sheet or a laminate thereof, and a non-elastic outer sheet 20 lying on the non-skin facing side and preferably formed of a non-elastic fibrous non-woven fabric, a non-elastic plastic sheet or a laminate thereof.

The absorbent structure 15 comprises a liquid-pervious top sheet 22 lying on the skin-facing side, a liquid-impervious bottom sheet 23 lying on the non-skin-facing side and a liquid-absorbent core 24 sandwiched between these two sheets 22, 23 and formed of a mixture of super-absorbent polymer particles and pulp fibers. An outer surface of the absorbent structure 21, i.e., the non-skin facing side of the bottom sheet 23, is fully or partially bonded to the inner surface of the chassis 14, e.g., by hot melt adhesive.

The top and bottom sheets 22, 23 extend outward beyond a periphery of the liquid-absorbent core 24 and are put in a face-to-face relationship and bonded together by hot melt adhesive outside the periphery of the liquid-absorbent core 24. Though not illustrated in FIGS. 1-4, it should be appreciated here that, to prevent sideways leakage of body waste, each of the portions of the top and bottom sheets 22, 23 extending outward beyond the side edges of the liquid-absorbent core 24 in the direction of the transverse axis Q (i.e., side flaps) may be provided with a plurality of elastic strands extending in the direction of the longitudinal axis P or provided with barrier cuffs formed of a liquid-impervious sheet member.

Figure 2:
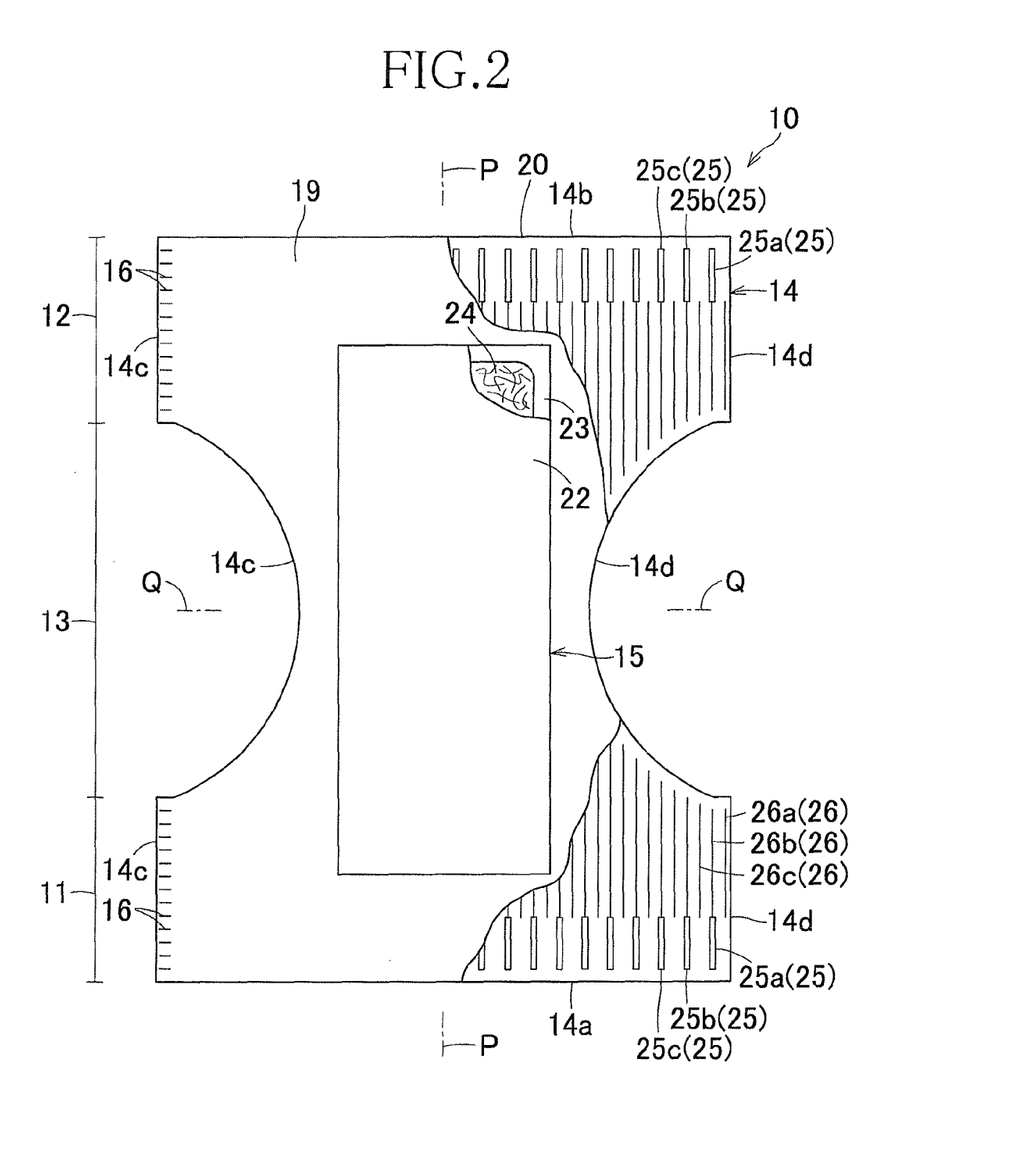
FIG. 2 is a partially cutaway plan view of the diaper in its flatly developed state after seams have been ripped open.
Figure 3:
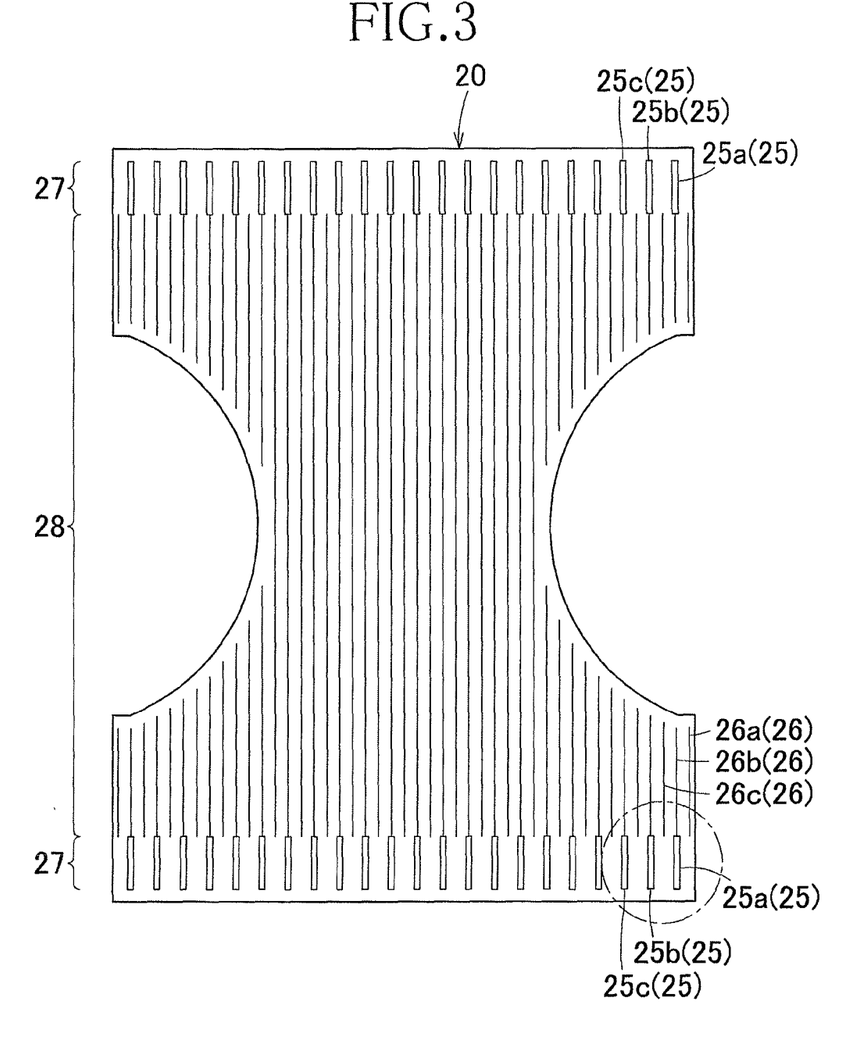
FIG. 3 is a diagram illustrating a coating pattern of adhesive lines.

As will be apparent from FIGS. 2 and 3, the inner sheet 19 and the outer sheet 20 constituting together the chassis or outer member 14 are bonded to each other by plural adhesive lines 25, 26 of hot melt adhesive coated on the inner surface of the outer sheet 20. Additionally or alternatively in further embodiments, such hot melt adhesive is coated on the outer surface of the inner sheet 19.

The adhesive lines 25, 26 comprise first adhesive lines 25 provided in vicinities of (i.e. adjacent to) the front and rear ends 14a, 14b so as to be intermittently arranged in the transverse axis Q, and second adhesive lines 26 extending in the direction of the longitudinal axis P across the crotch region 13 to the vicinities of (i.e. adjacent to) the first adhesive lines 25 in the front and rear waist regions 11, 12.

The first adhesive lines 25 comprise a plurality of independent adhesive lines 25a, 25b, 25c etc. extending in the direction of the longitudinal axis P and spaced from one another by a predetermined distance in the direction of the transverse axis Q. The second adhesive lines 26 also comprise a plurality of independent adhesive lines 26a, 26b, 26c etc. extending in the direction of the longitudinal axis P and spaced from one another by a predetermined distance in the direction of the transverse axis Q.

Front ends of the first adhesive lines 25 extending in the front waist region 11 and rear ends of the first adhesive lines 25 extending in the rear waist region 12 are located slightly inboard of (i.e. adjacent to) the front and rear ends 14a, 14b, respectively. The outermost pair of the second adhesive lines 26 are located respectively slightly inboard of (i.e. adjacent to) the associated side edges 14c, 14d in the front and rear waist regions 11, 12. Further, rear ends of the second adhesive lines 26 extending in a front half of the crotch region 13 and front ends of the second adhesive lines 26 extending in a rear half of the crotch region 13 are located respectively slightly inboard of (i.e. adjacent to) the associated side edges 14c, 14d of the crotch region 13. In other words, the first and second adhesive lines 25, 26 are neither present on nor extend up to the front and rear ends 14a, 14b as well as the side edges 14c, 14d in all front, rear and crotch regions 11, 12, 13. With such a unique arrangement, any regions stiffened due to hot melt adhesive would not come in contact with the wearer's skin and undesirably irritate the skin along the front and rear ends 14a, 14b as well as the side edges 14c, 14d.

In the chassis 14, the region in which the inner sheet 19 and the outer sheet 20 are joined together is divided into a first bonding region 27 coated with the first adhesive lines 25 and a second bonding region 28 coated with the second adhesive lines 26.

Figure 4:
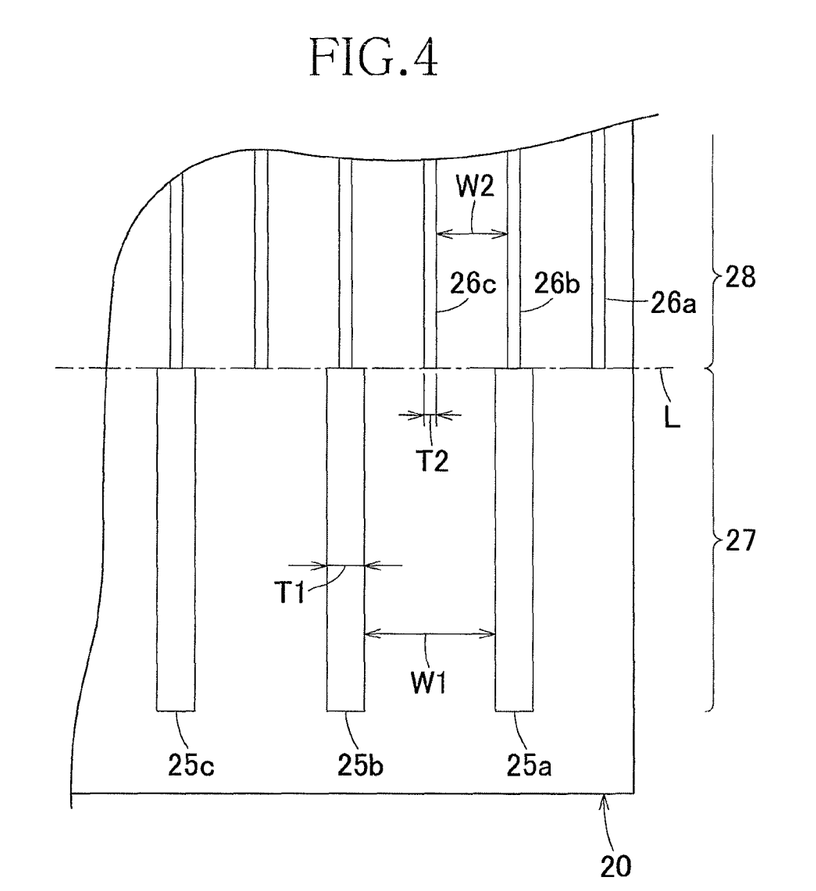
FIG. 4 is a diagram illustrating a part of FIG. 3 in an enlarged scale.

Referring to FIGS. 3 and 4, a width dimension T1 of the individual first adhesive line 25 in the direction of the transverse axis Q is larger than a width dimension T2 of the individual second adhesive line 26 in the direction of the transverse axis Q.

In general, a sheet member is stiffened in the region coated with hot melt adhesive and has a correspondingly high stiffness. Consequentially, when an elastic sheet is bonded to another sheet by hot melt adhesive, the elastic sheet will have its original elasticity deteriorated in the region coated with hot melt adhesive. Particularly, a stiffness value per unit area remarkably increases in the direction in which hot melt adhesive is continuously coated. The larger the amount hot melt adhesive coated, the higher the stiffness in the bonding region, and eventually the elasticity of the elastic sheet will be correspondingly deteriorated.

As described just above, the stiffness value per unit area of the first bonding region 27 in the direction of the longitudinal axis P is higher than the stiffness value per unit area of the second bonding region 28 in the direction of the longitudinal axis P, and the elasticity of the first bonding region 27 is lower than that of the second bonding region 28 because the first adhesive lines 25 are extensively coated with much greater amount of hot melt adhesive in comparison with the second adhesive lines 26.

The respective first bonding regions 27 lying in the upper areas of the front and rear waist regions 11, 12 have a relatively high stiffness and the elasticity in the direction of the longitudinal axis P appropriately restricted to facilitate these regions to be held by fingers and to be pulled upward when the diaper 10 is put on the wearer's body. In contrast, in the second bonding region 28 lying in the lower areas of the front and rear waist regions 11, 12 and the crotch region 13, stiffness is relatively low and elasticity is not significantly restricted. The second bonding region 28 having its elasticity maintained sufficiently high can smoothly follow the movement of the wearer's thighs and/or inguinal region without getting wrinkles.

Specifically, to achieve the effect as has been described above, a stiffness value per unit area of the first bonding region 27 in the direction of the longitudinal axis P is preferably in a range of about 1.0 to about $1.3 \times 10^{-4}$ N×m$^2$/m, and a stiffness value per unit area of the second bonding region 28 in the direction of the longitudinal axis P is preferably in a range of about 0.4 to about $0.7 \times 10^{-4}$ N×m²/m.

A distance dimension W1 between each pair of the adjacent first adhesive lines 25a, 25b is larger than a distance dimension W2 between each pair of the adjacent second adhesive lines 26a, 26b.

More specifically, when the width dimension T1 of the individual first adhesive line 25 is in a range of about 2.0 to about 3.5 mm and the width dimension T2 of the individual second adhesive line 26 is in a range of about 0.5 to about 2.0 mm, the distance dimension W1 between each pair of the first adhesive lines 25 being adjacent in the direction of the transverse axis Q is preferably in a range of about 5.5 to about 7.5 mm, and the distance dimension between each pair of the second adhesive lines 26 being adjacent in the direction of the transverse axis Q is preferably in a range of about 3.5 to about 5.5 mm in order to achieve the effect as has been described above. This is for the reason that, so far as the width dimensions T1, T2 and the distance dimensions W1, W2 of the first and second adhesive lines 25, 26 are in the above-indicated preferred ranges, the correlation between the stiffness value per unit area and the elasticity in the first and second bonding regions 27, 28 is not affected even if the number of the second adhesive lines 26 is larger than the number of the first adhesive lines 27.

Even if the width dimensions T1, T2 and the distance dimensions W1, W2 of the first and second adhesive lines 25, 26 are substantially the same (i.e., even if the stiffness values per unit area of the first bonding region 27 and the second bonding region 28 are substantially the same), the waist regions of the diaper 10 put on the wearer's body still curve toward the wearer's skin in the vicinity of (i.e. adjacent to) the boundary L (FIG. 4) between the first bonding region 27 and the second bonding region 28. This is for the reason that some or all of the second adhesive lines 26 are not contiguous to any of the first adhesive lines 25 and, in consequence, stiffness due to hot melt adhesive is locally interrupted along the boundary L. The above-described differential stiffness between the first bonding region 27 and the second bonding region 28 further facilitates the waist regions of the diaper 10 to curve inward toward the wearer's skin in a vicinity of the boundary L between these first and second bonding regions 27, 28.

Figure 5:
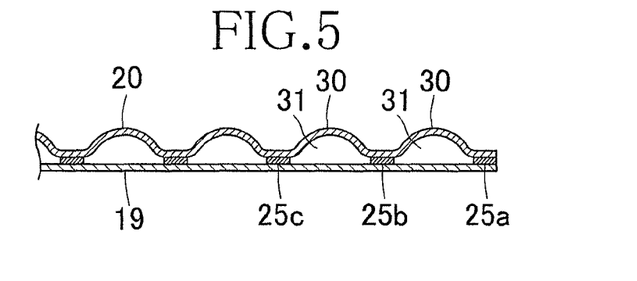
FIG. 5 is a sectional view taken along the line V-V in FIG. 1.
Figure 6:
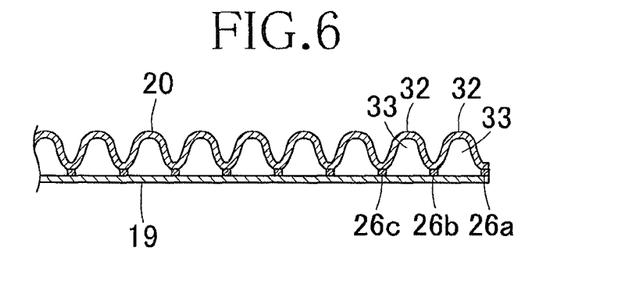
FIG. 6 is a sectional view taken along the line VI-VI in FIG. 1.

FIG. 5 is a sectional view taken along the line V-V in FIG. 1 and FIG. 6 is a sectional view taken along the line VI-VI in FIG. 1.

In the first bonding region 27, as will be apparent from FIG. 5, between each pair of the first adhesive lines 25a, 25b, 25c, etc. being successively adjacent in the direction of the transverse axis Q, the outer sheet 20 is formed with first outwardly convex segments 30 and, between these first convex segments 30 and the inner sheet 19, a plurality of first channels 31 extending in the direction of the longitudinal axis P are defined. Openings of the respective first channels 31 are formed slightly inboard of the front and rear ends 14a, 14b of the front and rear waist regions 11, 12, respectively.

These first channels 31 formed in the first bonding region 27 in the manner as has been described above serve not only to improve cushioning properties but also, particularly when the inner sheet 19 is moisture-pervious, to let out moisture generated within the diaper 10 through the first channels 31 and thereby to prevent efficiently the inside of the diaper 10 from becoming stuffy.

In the second bonding region 28, now referring to FIG. 6, between each pair of the second adhesive lines 26a, 26b, 26c, etc. being successively adjacent in the direction of the transverse axis Q, the outer sheet 20 is formed with second outwardly convex segments 32 (See FIG. 1) and, between these second convex segments 32 and the outer sheet 20, a plurality of second channels 33 extending in the direction of the longitudinal axis P are defined.

Slightly inboard of (i.e. adjacent to) the opposite side edges 14c, 14d of the crotch region extending into the front and rear waist regions 11, 12, openings of the second channels are formed. These openings are provided around the peripheries of the leg openings, as may be seen in FIG. 1. The second channels 33 formed in the second bonding region 28 in this manner serve not only to improve cushioning properties but also, particularly when the inner sheet 19 is moisture-pervious, to let out moisture generated within the diaper 10 from the openings of the second channels 33 and/or from the openings of the first channels 31 after flowing through both the second channels 33 and the first channels 31 and thereby to efficiently prevent the inside of the diaper 10 from becoming stuffy.

As has previously been described, the distance dimension W1 of the first adhesive lines 25 being adjacent in the direction of the transverse axis Q is larger than the distance dimension W2 of the second adhesive lines 26 being adjacent in the direction of the transverse axis Q and, consequently, the first channel 31 has an inner diameter or an internal area larger than that of the second channel 33. Correspondingly, it is possible for the first channels 31 to let out much more amount of moisture generated within the diaper 10 through the openings thereof.

To form a plurality of these channels 31, 33 between the inner sheet 19 and the outer sheet 20 in this way, the outer sheet 20 is previously dimensioned in the direction of the transverse axis Q to be larger than the width dimension of the inner sheet 19 in the direction of the transverse axis Q. In the course of forming the outer member 14, the inner sheet 19 is stretched to the width dimension of the outer sheet 20 and then these both sheets 19, 20 are bonded by the first and second adhesive lines 25, 26. Upon contraction of the inner sheet 19, the outer sheet 20 is formed with the first and second outwardly convex segments 30, 32.

While the second adhesive lines 28 extend across the crotch region 13 and into the front and rear waist regions 11, 12 so far as this embodiment is concerned, it is possible to implement the second bonding region 28 so as to be formed exclusively in the front and rear waist regions 11, 12, or only in any one of the front and rear waist regions 11, 12.

Second Embodiment

Figure 7:
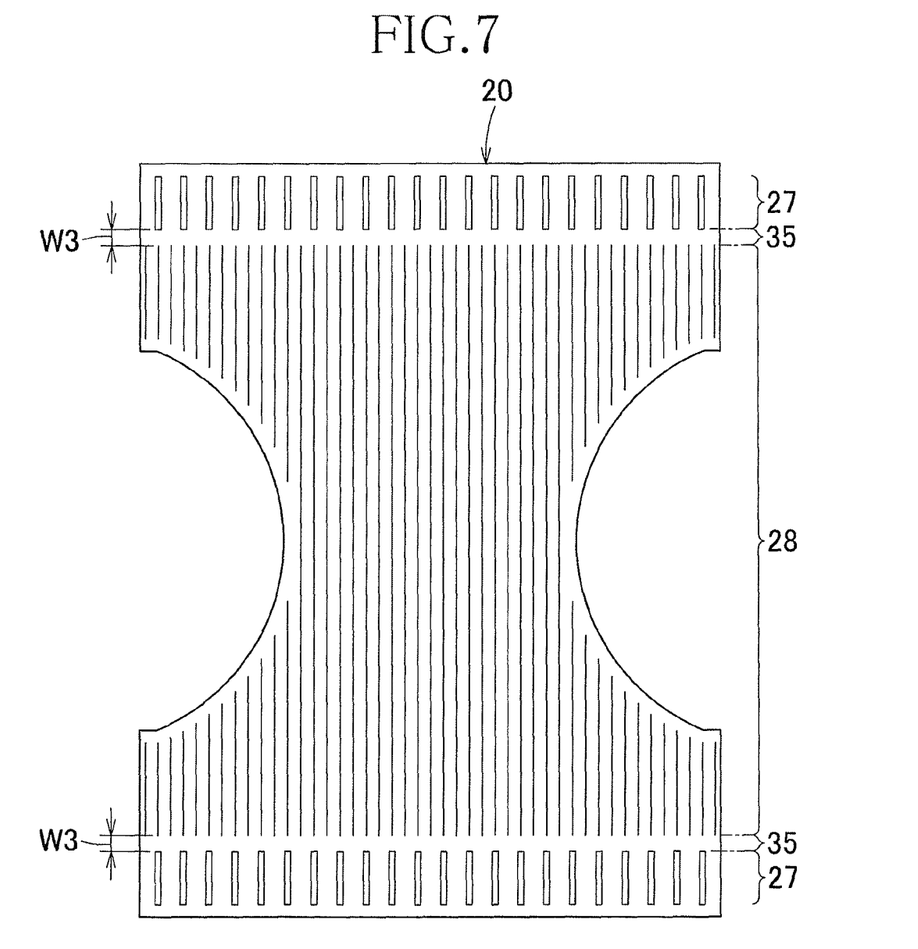
FIG. 7 is a view similar to FIG. 3, showing a coating pattern of adhesive lines according to a second embodiment of the present invention.
Figure 8:
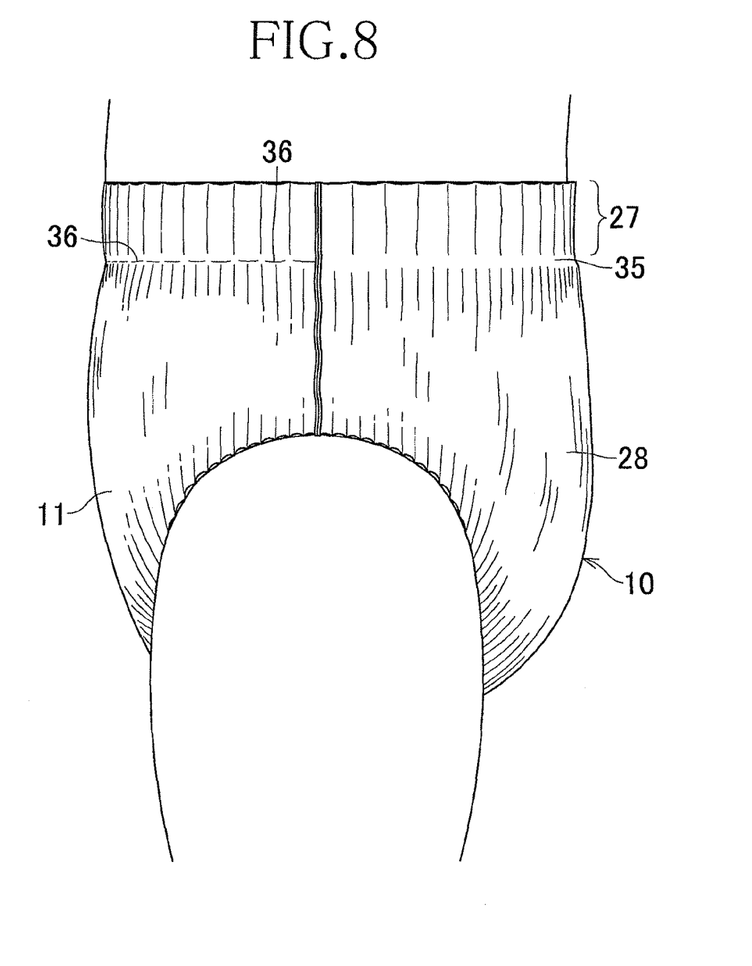
FIG. 8 is a diagram showing the diaper according to the second embodiment put on the wearer's body.

FIG. 7 is a view similar to FIG. 3, showing the diaper 10 according to a second exemplary embodiment and FIG. 8 is a diagram schematically illustrating the diaper 10 according to the second embodiment put on the wearer's body.

Referring to FIG. 7, the first bonding region 27 and the second bonding region 28 are spaced from each other by a predetermined distance in the direction of the longitudinal axis P to define non-bonding regions 35 extending in the direction of the transverse axis Q and not coated with hot melt adhesive.

Taking account of the previously described relationship between the first and second bonding regions 27, 28, stiffness values per unit area in the first and second bonding regions 27, 28 and the non-bonding regions 35 free from hot melt adhesive may be correlated in the following relationship the first bonding region 27>the second bonding region 28>the non-bonding region 35. Elasticity of these regions may be correlated in the following relationship the non-bonding region 35>the second bonding region 28>the first bonding region 27.

As shown by FIG. 7, the non-bonding region 35 circumferentially comes in contact with the wearer's waist at a level corresponding to a substantially middle region of the wearer's belly (i.e., the position of the wearer's bellybutton). The non-bonding region 35 has a stiffness lower than those of the first and second bonding regions 27, 28 respectively lying above and below the non-bonding region 35 and easily curves toward the wearer's body.

The substantially middle region of the wearer's belly, along which the non-bonding region 35 comes in contact with the wearer's skin, corresponds to the region which should be smoothly bent inward as the wearer bends him- or herself forward or crawls on his or her belly. From this viewpoint, the non-bonding region 35 of a relatively low stiffness put in contact with such region of the wearer's body facilitates the wearer's movement such as bending forward or crawling on his or her belly. Even if none of the non-bonding regions 35 is provided, a more or less similar effect can be achieved by the region in the vicinity of the boundary L between the first and second bonding regions 27, 28 coming in contact with the above-described region of the wearer's body as the first embodiment is the case.

The first and second adhesive lines 25, 26 extending in the direction of the longitudinal axis P form the diaper 10 as a whole with a plurality of large and small gathers extending in the direction of the longitudinal axis P (similar to convex segments 30, 32 in the first embodiment). However, the non-bonding region 35 is not formed with such gathers. The non-bonding region 35 is rather formed with a plurality of wrinkles 36 extending in the direction of the transverse axis Q as the wearer bends him- or herself forward or crawls on his or her belly, so that the first bonding region 27 and the second bonding region 28 might overlap or touch each other.

To achieve the effect as has been described just above, a dimension W3 of the non-bonding region 35 in the direction of the longitudinal axis P is preferably in a range of 2 to 5 mm and a stiffness value per unit area thereof in the direction of the longitudinal axis P is preferably in a range of about 0.2 to about $0.4 \times 10^{-4}$ N×m²/m. A dimension W3 of the non-bonding region 35 below 5 mm is preferable, to prevent a plurality of wrinkles 36 extending in the direction of the transverse axis Q causing the diaper 10 to contract in the direction of the longitudinal axis P, which could affect the diaper being held at the desired position around the wearer's waist.

Stiffness in the first and second bonding regions 27, 28 and in the non-bonding region 35 was measured by a method as will be described below.

Measuring Method of Stiffness Value per Unit Area

Test pieces each having a width of 100 mm and a length of 100 mm cut out from the product were set on Pure Bending Tester KES FB-2 manufactured by KATO TECH CO., LTD. in Japan so that each of the test pieces may be bent vertically with respect to the MD direction (i.e., in the direction of the longitudinal axis P) and the bending stiffness was measured.

Each of the test pieces comprises the outer sheet 20 formed of non-elastic spun bonded non-woven fabric (having a basis weight of 17 g/m²) and the inner sheet 19 formed of an elastic spun bonded non-woven fabric (having a basis weight of 30 g/m²) made of polypropylene/polyurethane mixture, wherein the inner sheet 19 is bonded in a state stretched at a ratio of 2.4 to the outer sheet 20 by hot melt adhesive so as to include the first and second bonding regions 27, 28 and the non-bonding region 35.

In the first bonding region 27, each of the first adhesive lines 25 has the width dimension T1 of 3 mm and each pair of the adjacent first adhesive lines 25 has the distance dimension W1 of 7 mm. In the second bonding region 28, each of the second adhesive lines 26 has the width dimension T2 of about 1 mm and each pair of the adjacent second adhesive lines 26 has the distance dimension W2 of 5 mm. The non-bonding region 35 has the dimension W3 of 5 mm.

In this measurement, the test piece mounted on the tester is automatically clamped at intervals of 1 cm (at the respective middle points of the distance dimensions W1, W2, respectively, in the first and second bonding regions 27, 28) and the bending moment (stiffness value per unit area) in the direction of the longitudinal axis P was measured at a predetermined curvature factor. Specifically, the bending moment was determined at the curvature factor of 0.1 to 0.3 cm$^{-1}$ at which the test piece begins to bend.

The measurement result is indicated in TABLE 1. Measurement result 1 indicates the stiffness value per unit area obtained in the first bonding region 27, measurement result 2 indicates the stiffness value per unit area obtained in the second bonding region 28 and measurement result 3 indicates the stiffness value per unit area obtained in the non-bonding region 35.

TABLE 1

|  | Bending moment(stiffness value per unit area) ($10^{-4}$ N × m²/m) |
| --- | --- |
| Measurement result 1 | 1.3008 |
| Measurement result 2 | 0.6106 |
| Measurement result 3 | 0.3269 |

As the measurement result indicates, the bending moment (i.e., stiffness value per unit area) is highest in the first bonding region 27 and becomes lower in the second bonding region 28 and the non-bonding region 35 in this order.

Stock materials for the respective component members of the diaper 10 such as the chassis 14 and the absorbent structure 15 are not limited to those described in this specification and any other suitable materials known in the relevant technical field may be used without any limitation. The diaper 10 is not limited to the pants-type disposable diaper and the present invention may be implemented in the form of a so-called open-type diaper in which the side seams of the front and rear waist regions 11, 12 are not previously joined together. Furthermore, the invention may be implemented in the form of a diaper comprising separately prepared front and rear waist regions 11, 12 which are then joined together by a crotch region 13.

The aspects of the present invention described above may be arranged in at least the following item(s):

(i) A disposable diaper (10) having a longitudinal axis (P) and a transverse axis (Q), a skin-facing side and a non-skin-facing side, comprises: a first waist region (11), a second waist region (12), a crotch region (13) extending between the first and second waist regions, a waist-opening (17) and a pair of leg-openings (18) wherein at least the first waist region of the first and second waist regions is elastic, wherein:

the first waist region includes a non-elastic sheet (20) lying on the non-skin-facing side and an elastic sheet (19) lying on the skin-facing side;

the non-elastic sheet and the elastic sheet are joined together along plural adhesive lines extending in a direction of the longitudinal axis and spaced from one another in a direction of the transverse axis;

the adhesive lines comprise first adhesive lines (25) extending from or from adjacent to a peripheral edge of the waist-opening toward the crotch region and defining a first bonding region (27), and second adhesive lines (26) extending from the crotch region toward the first adhesive lines and defining a second bonding region (28); and at least some of the second adhesive lines are noncontiguous to any of the first adhesive lines in the direction of the longitudinal axis.

(xi) A disposable diaper (10) having a longitudinal axis (P) and a transverse axis (Q), a skin-facing side and a non-skin-facing side, comprises:

a first waist region (11), a second waist region (12), a crotch region (13) extending between the first and second waist regions, a waist-opening (17) and a pair of leg-openings (18), wherein at least the first waist region of the first and second waist regions is elastic, and includes two sheets (19, 20), at least one of which is an elastic sheet, joined together by adhesive in a first bonding region (27) adjacent a peripheral edge of the waist-opening and in a second bonding region (28) adjacent the crotch region;

a stiffness value per unit area of the first bonding region is greater than that of the second binding region; and a boundary (L, 35) between the first bonding region and the second bonding region where the stiffness value per unit area abruptly changes is adapted to be, in use, at a level corresponding to the belly button of a wearer of the diaper to cause the first waist region to curve along the boundary toward the wearer in response to movements of the wearer.

The aspect(s) of the present invention described in the above items (i) and (xi) may provide one or more of the following advantageous effect(s):

(a) With such an arrangement, when the diaper put on the wearer's body, the region defined in the vicinity of the boundary between the first bonding region and the second bonding region is apt to be folded inward. Particularly, when this region defined in the vicinity of the boundary is put in contact with the wearer's belly at the middle level thereof, such feature facilitates the wearer to bend him- or herself forward or to crawl on his or her belly.

Additionally, one or more of the following embodiments are provided in accordance with further aspects:

(ii) A region defined adjacent to a boundary (L) between the first bonding region and the second bonding region is adapted to be folded inward in use.

(iii) A width dimension (T1) of each first adhesive line in the direction of the transverse axis is larger than that (T2) of each second adhesive line, and a stiffness value per unit area of the first bonding region in the direction of the longitudinal axis is higher than that of the second bonding region.

(iv) The elastic sheet is moisture-pervious, a plurality of tubular channels (31, 33) extending in the direction of the longitudinal axis are defined between each pair of the adhesive lines successively adjacent in the direction of the transverse axis, a distance dimension (W1) between each pair of the first adhesive lines adjacent in the direction of said transverse axis is larger than (W2) that between each pair of the adjacent second adhesive lines and the channel (31) formed in the first bonding region is larger than the channel (33) formed in the second bonding region.

(v) The first bonding region and the second bonding region are spaced from each other in the direction of the longitudinal axis by a non-bonding region (35) extending in the direction of the transverse axis.

(vi) The adhesive lines are formed of hot melt adhesive.

(vii) A stiffness value per unit area of the first bonding region (27) in the direction of the longitudinal axis is in a range of 1.0 to $1.3 \times 10^{-4}$ N×m$^2$/m, and a stiffness value per unit area of the second bonding region (28) in the direction of the longitudinal axis is in a range of 0.4 to $0.7 \times 10^{-4}$ N·×m$^2$/m.

(viii) A width dimension (T1) of each first adhesive line is in a range of 2.0 to 3.5 mm, a width dimension (T2) of each second adhesive line is in a range of 0.5 to 2.0 mm, a distance dimension (W1) between each pair of the first adhesive lines being adjacent in the direction of the transverse axis is in a range of 5.5 to 7.5 mm, and a distance dimension (W2) between each pair of the second adhesive lines being adjacent in the direction of the transverse axis is in a range of 3.5 to 5.5 mm.

(ix) Stiffness values per unit area in the first and second bonding regions and the non-bonding regions are correlated in the following relationship: the first bonding region>the second bonding region>the non-bonding region, and elasticity thereof are correlated in the following relationship: the non-bonding region>the second bonding region>the first bonding region.

(x) A dimension (W3) of the non-bonding region in the direction of the longitudinal axis is in a range of 2 to 5 mm, and a stiffness value per unit area thereof in the direction of the longitudinal axis is in a range of 0.2 to $0.4 \times 10^{-4}$ N×m$^2$/m.

(xii) The adhesive bonding the two sheets of the first waist region includes a plurality of first adhesive lines (27) in the first bonding region and defining the stiffness value per unit area of the first bonding region; and a plurality of second adhesive lines (28) in the second bonding region and defining the stiffness value per unit area of the second bonding region.

(xiii) A width dimension (T1) of each first adhesive line in the direction of the transverse axis is larger than that (T2) of each second adhesive line.

(xiv) A distance dimension (W1) between each pair of the first adhesive lines adjacent in the direction of the transverse axis is larger than that (W2) between each pair of the adjacent second adhesive lines.

(xv) The first bonding region and the second bonding region are spaced from each other in the direction of the longitudinal axis by a non-bonding region (35) extending in the direction of the transverse axis.

(xvi) The stiffness value per unit area of the first bonding region in the direction of the longitudinal axis is in a range of 1.0 to $1.3 \times 10^{-4}$ N·m$^2$/m, and the stiffness value per unit area of the second bonding region in the direction of the longitudinal axis is in a range of 0.4 to $0.7 \times 10^{-4}$ N×m$^2$/m.

(xvii) A width dimension (T1) of each first adhesive line is in a range of 2.0 to 3.5 mm, and a width dimension (T2) of each second adhesive line is in a range of 0.5 to 2.0 mm.

(xviii) A distance dimension (W1) between each pair of the first adhesive lines being adjacent in the direction of the transverse axis is in a range of 5.5 to 7.5 mm, and a distance dimension (W2) between each pair of the second adhesive lines being adjacent in the direction of the transverse axis is in a range of 3.5 to 5.5 mm.

(xix) The stiffness values per unit area in the first and second bonding regions and the non-bonding region are correlated in the following relationship: the first bonding region>the second bonding region>the non-bonding region, and elasticity thereof are correlated in the following relationship: the non-bonding region>the second bonding region>the first bonding region.

(xx) A dimension (W3) of the non-bonding region in the direction of the longitudinal axis is in a range of 2 to 5 mm, and a stiffness value per unit area thereof in the direction of the longitudinal axis is in a range of 0.2 to $0.4 \times 10^{-4}$ N·xm$^2$/m.

According to the embodiments in the above (ii) to (ix) and (xii) to (xx), one or more of the advantageous effect(s) set forth at (a) is/are better ensured. Further advantageous effects of the respective embodiments may be obtained as discussed in the respective descriptions.

The terms "first" and "second" herein are used merely for distinguishing between similar elements. Furthermore, the wording "first waist region" herein means one of the front and rear waist regions, and the wording "second waist region" herein means the other.

The terms "in the vicinity of", "adjacent to" and "lie slightly inboard of" herein are used to define the locations of respective features relative to one another, which features do not contact one another but lie close to one another.

The invention claimed is:

1. A disposable diaper having a longitudinal axis and a transverse axis, a skin-facing side and a non-skin-facing side, said diaper comprising:
    a first waist region, a second waist region, a crotch region extending between said first and second waist regions,
    a waist-opening and a pair of leg-openings,
    wherein
    at least said first waist region of said first and second waist regions is elastic, and includes two sheets, at least one of which is an elastic sheet, said two sheets joined together by adhesive in a first bonding region adjacent a peripheral edge of said waist-opening and in a second bonding region adjacent said crotch region;
    the first bonding region comprises a plurality of first adhesive lines which are straight and extend linearly in a direction of the longitudinal axis,
    the second bonding region comprises a plurality of second adhesive lines which are straight and extend linearly in the direction of the longitudinal axis,
    a width dimension of each of said first adhesive lines in a direction of said transverse axis is larger than that of each of said second adhesive lines,
    a distance between each pair of said first adhesive lines adjacent in the direction of said transverse axis is larger than that between each pair of the adjacent second adhesive lines,
    the first and second adhesive lines define stiffness values per unit area of the first and second bonding regions, respectively,
    the stiffness value per unit area of the first bonding region is greater than that of the second bonding region,
    the first waist region is configured to be curved along a boundary toward the skin-facing side in response to movements of a wearer of the diaper, and
    the boundary extends between said first bonding region and said second bonding region where the stiffness value per unit area abruptly changes and is configured to be, in use, at a level corresponding to the belly button of the wearer of the diaper.

2. The diaper defined by claim 1, wherein
    said first bonding region and said second bonding region are spaced from each other in the direction of said longitudinal axis by a non-bonding region extending in the direction of said transverse axis.

3. The diaper defined by claim 1, wherein
    the stiffness value per unit area of said first bonding region in the direction of said longitudinal axis is in a range of 1.0 to $1.3 \times 10^{-4}$ N×m$^2$/m, and
    the stiffness value per unit area of said second bonding region in the direction of said longitudinal axis is in a range of 0.4 to $0.7 \times 10^{-4}$ N×m$^2$/m.

4. The diaper defined by claim 1, wherein
    the width dimension of each said first adhesive line is in a range of 2.0 to 3.5 mm, and
    the width dimension of each said second adhesive line is in a range of 0.5 to 2.0 mm.

5. The diaper defined by claim 1, wherein
    the distance between each pair of said first adhesive lines being adjacent in the direction of the transverse axis is in a range of 5.5 to 7.5 mm, and
    the distance between each pair of the second adhesive lines being adjacent in the direction of the transverse axis is in a range of 3.5 to 5.5 mm.

6. The diaper defined by claim 2, wherein
    the stiffness value per unit area in said second bonding region is greater than a stiffness value per unit area in said non-bonding region,
    elasticity of said non-bonding region is greater than elasticity of said second bonding region, and
    the elasticity of said second bonding region is greater than elasticity of said first bonding region.

7. The diaper defined by claim 2, wherein a dimension of said non-bonding region in the direction of said longitudinal axis is in a range of 2 to 5 mm, and a stiffness value per unit area of said non-bonding region in the direction of said longitudinal axis is in a range of 0.2 to $0.4 \times 10^{-4}$ N×m$^2$/m.

8. The diaper defined by claim 6, wherein said non-bonding region is free of said adhesive and extends between two side edges of the said first waist region, the two side edges opposite each other in the direction of said transverse axis.

* * * * *